United States Patent [19]
Glombik et al.

[11] Patent Number: 5,610,151
[45] Date of Patent: Mar. 11, 1997

[54] MONOMERIC BILE ACID DERIVATIVES, PROCESSES FOR THEIR PREPARATION AND THE USE OF THESE COMPOUNDS AS MEDICAMENTS

[75] Inventors: Heiner Glombik, Hofheim; Alfons Enhsen, Büttelborn; Werner Kramer, Mainz; Günther Wess, Erlensee, all of Germany

[73] Assignee: Hoechst Aktiengesellschaft, Frankfurt am Main, Germany

[21] Appl. No.: 238,749

[22] Filed: May 5, 1994

[30] Foreign Application Priority Data

May 8, 1993 [DE] Germany ............... 43 15 439.5

[51] Int. Cl.$^6$ ............... A61K 31/585; C07J 17/00
[52] U.S. Cl. ............... 514/172; 514/177; 514/182; 514/255; 514/299; 536/5; 536/6; 536/6.2; 546/112; 549/223; 552/506; 552/549; 552/550; 552/551
[58] Field of Search ............... 514/177, 172, 514/182, 299, 255; 536/5, 6, 6.2; 549/223; 552/506, 550, 549, 551; 546/112

[56] References Cited

U.S. PATENT DOCUMENTS

| | | | |
|---|---|---|---|
| 4,217,279 | 8/1980 | Kaiser | 200/239.55 R |
| 5,250,524 | 10/1993 | Kramer et al. | 514/177 |

FOREIGN PATENT DOCUMENTS

| | | |
|---|---|---|
| 2025294 | 9/1990 | Canada . |
| 2085830 | 12/1992 | Canada . |
| 0417725A2 | 9/1990 | European Pat. Off. . |
| 0489423A1 | 6/1992 | European Pat. Off. . |
| 0548793A2 | 12/1992 | European Pat. Off. . |
| 2444686 | 7/1980 | France . |
| 1119263 | 12/1961 | Germany . |

OTHER PUBLICATIONS

Murata et al., "Determination of Sulfated and Nonsulfated Bile Acids in Serum by Mass Fragmentography," *Steroids*, vol. 42, No. 5, Nov. 1983, pp. 575–592.

De Witt et al., "Effects of sulfation patterns on intestinal transport of bile salt sulfate esters," Chemical Abstracts, vol. 92, No. 8, Abstract No. 073345, 1980, p. 404.

Wess, et al., "Specific Inhibitors of Ileal Bile Acid Transport," *Journal of Medicinal Chemistry*, vol. 27, No. 7, Apr. 1, 1994, pp. 873–875.

Bartholomew, et al., "The effect of 3–sulfation and taurine conjugation on the uptake of chendeoxycholic acid by rat hepatocytes," Chemical Abstracts, vol. 100, No. 1, Jan. 2, 1984, p. 344.

Ammon et al., "Effects of Sulfodeoxychloate on rat and rabbit small intestine," Chemical Abstracts, vol. 103, No. 1, Jul. 8, 1985, p. 404.

Mazumder et al., "Bile acid transformations by Alcaligenes recti," *Steroids*, vol. 58, No. 2, Feb. 1993, pp. 79–86.

Babcoc, et al., "Reductive Methylation of Steroid Ketones," *Journal of the American Chemical Society*, vol. 74, No. 21, Nov. 5, 1952, pp. 5472–5474.

De Weert et al., "Quantitative determination of fecal bile acids as their methyl ether methyl esters by the repetitive scan technique," Chemical Abstracts, vol. 95, No. 3, Jul. 20, 1981.

Pellicciari et al., "Bile Acids with a Cyclopropyl–Containing Side Chain. 1. Preparation and Properties of 3α, 7β–Dihydroxy–22,23–methylene–5β–cholan–24–oic Acid," *Journal of Medicinal Chemistry*, vol. 27, No. 6, Jun. 6, 1984, pp. 746–749.

Hill et al., *Dictionary of Steroids, Indexes*, 1991, pp. 386–387.

Redel et al., "Amines cycliques des acides biliares. Première partie:Monoamines,"*Bulletin de la Societe Chimique de France (Memoires)*, 1949, pp. 877–883.

Müllner, et al., "Synthesis of Affinity Chromatography and Electrophoresis Matrices for the Purification of Bile Acid Transport Proteins," *Chromatographia*, vol. 34, No. 5, Jan. 1993, pp. 819–822.

Crawford et al., "Physical and biological properties of fluorescent dansylated bile salt derivatives: the role of steroid ring hydroxylation," *Biochimica et biophysica Acta*, vol. 1085, No. 2, Apr. 26, 1991, pp. 223–234.

Ho et al., "Utilising bile acid carrier mechanisms to enhance liver and small intestine absorption," Chemical Abstracts, vol. 110, No. 4, Jan. 23, 1989, p. 330.

Sherman et al., "Hepatic transport of fluorescent molecules: in vivo studies using intravital TV microscopy," *Hepatology*, vol. 6, No. 3, May–Jun. 1986, pp. 444–449.

Yasuo et al., "Basic bile acids. I. Synthesis and configuration of 3. alpha–aminocholanic acid," Chemical Abstract, vol. 55, No. 4, Feb. 20, 1961, pp. 3648.

Kramer, et al., "Liver–specific Drug Targeting by Coupling to Bile Acids," *The Journal of Biological Chemistry*, vol. 267, No. 26, Sep. 15, 1992, pp. 18598–18604.

Wess et al., "Synthesis of Bile Acid—Drug Conjugates: Potential Drug—Shuttles for Liver Specific Targeting," *Tetrahedron Letters*, vol. 34, No. 5, Jan. 1993, pp. 819–822.

Bandiera et al., "A Convenient Procedure for the Synthesis of Ursodeoxycholic Acid Sulfated Derivates," *Synthetic Communications*, vol. 17, No. 9, 1987, pp. 1111–1117.

(List continued on next page.)

*Primary Examiner*—C. Warren Ivy
*Assistant Examiner*—Raymond Covington
*Attorney, Agent, or Firm*—Finnegan, Henderson, Farabow, Garrett & Dunner, L.L.P.

[57] ABSTRACT

Monomeric bile acid derivatives, processes for their preparation and the use of these compounds as medicaments Monomeric bile acid derivatives of the formula I $$Z-X-GS \qquad\qquad I,$$

in which GS, X and Z have the meanings given, and processes for their preparation are described. The compounds have useful pharmacological properties and can therefore be used as medicaments.

4 Claims, No Drawings

OTHER PUBLICATIONS

Wess et al., "Evaluation of the Bile Acid Transporter in Enhancing Intestinal Permeability to Renin–Inhibitory Peptides," *Journal of Drug Targeting*, vol. 1, No. 4, Dec. 1993, pp. 347–359.

Kocian et al., "Effect of oral calcium administration on the cholesterol and phospholipid serum levels," Chemical Abstracts, vol. 73, No. 3, 1970, p. 220.

Morishita et al., "Synthesis and Hypolipidemic Activity of 2–Substituted Isobutyric Acid Derivatives," *Journal of Medicinal Chemistry*, vol. 31, No. 6, 1988, pp. 1205–1209.

Chapman, Jr., et al., "Hypolipidemic Activity of Phthalimide Derivatives V: Reduced and Hydrolytic Products of Simple Cyclic Imides," *Journal of Pharmaceutical Sciences*, vol. 73, No. 10, Oct. 1984, pp. 1482–1484.

Villegas–Navarro, "9–Anthracenecarboxylic acid and hematological and biochemical variables in the rat," Chemical Abstracts, vol. 112, No. 21, May, 1990, p. 230.

Greisen et al., "Inhibition of $^3$H–Glibenclamide Binding to Sulfonylurea Receptors by Oral Antidiabetics," *Arzneimittel Forschung Drug Research*, vol. 35, No. 4, 1985, pp. 707–712.

Hardison et al., "Specificity of an $Na^+$–dependent taurocholate transport site in isolated rat hepatocytes," *American Journal of Physiology: Gastrointestinal and Liver Physiology*, vol. 9, No. 5, May 1984, pp. G477–G483.

Palmieri et al., "Clinical Research into the Hypolipemic and Platelet Antiaggregant Activity of Plafibride, Carried out in Double–blind Conditions and in Comparison with Clofibrate," *Arzneimittel Forschung Drug Research*, vol. 31, No. 10a, 1981, pp. 1863–1866.

Quackenbush et al., "Arylsulfonate Esters of Fatty Alcohols. II. Structural Relation to Hypocholesterolemic Acitivity," *Artery*, vol. 3, No. 6, 1977, pp. 553–575.

S. Yamada e tal., "Mild Oxidation of Aldehydes to the Corresponding Carboxylic Acids and Esters: Alkaline Iodine Oxidation Revisited," Tetrahedron Letters, Bd. 33, Nr. 30, Oxford, G. B., pp. 4329–4332 (1992).

G. Wess et al., "Preparation of 3α— and 3β–(ω–aminoalkoxy)–7α,12α–dihydroxy–5β–cholanoic acid esters: Versatile Shuttles for Drug Targeting," Tetrahedron Letters, Bd. 34, Nr. 5, Oxford, G. B., pp. 817–818 (Jan. 1993).

G. Wess et al., "Modified Bile Acids: Preparation of 7α,12α–dihydroxy–3β– and 7α,12α–dihydroxy–3α–(2–hydroxyethoxy)–5β–cholanic Acid and Their Biological Activity," Tetrahedron Letters, Bd. 33, Nr. 2, Oxford, G. B., pp. 195–198 (1992).

W. Zhou et al., "Studies on Steroidal Plant–Growth Regulator 25. Concise Stereoselective Construction of Sidechain of Brassinosteroid from the Intact Sidechain of Hyodeoxycholic Acid: Formal Synthesis of Brassinolide, 25–methylbrassinolide, 26,27–bisnorbrassinolide and Their Related Compounds," Tetrahedron Letters, Bd. 48, Nr. 10, Oxford, G. B., pp. 1837–1852 (1992).

W. Kramer et al., "Liver–specific Drug Targeting by Coupling to Bile Acids," Chemical Abstracts, vol. 117, No. 12, abstract no. 118326, (Sep. 21, 1992).

MONOMERIC BILE ACID DERIVATIVES, PROCESSES FOR THEIR PREPARATION AND THE USE OF THESE COMPOUNDS AS MEDICAMENTS

Bile acids are synthesized in the liver from cholesterol in several enzymatic steps. They are stored in the gall bladder, from which they are secreted with the bile into the small intestine. They fulfill important physiological functions there during the digestion process, for example as cofactors or pancreatic lipases and as natural detergents for absorption of fats and fat-soluble vitamins. The greatest proportion of bile acids returns to the liver from the small intestine via the portal vein blood by active and passive transportation processes.

Polymers which bind bile acids have been employed as therapeutics for a relatively long time. They are used for diseases where inhibition of the absorption of bile acid is desirable. In cases of an increased blood cholesterol level, increased synthesis of bile acids from cholesterol can be induced in the liver by reducing the amount of bile acids in the enterohepatic circulation. This leads to an increased LDL cholesterol uptake from the blood into the liver and an accelerated LDL catabolism. The effect achieved is a reduction in the atherogenic LDL cholesterol in the blood.

The polymers used as medicaments for this purpose, for example cholestyramine or colestipol, must be administered in very high daily doses of 12 to 30 g. In addition to the high dosage, the taste and smell make acceptance by patient and doctor more difficult.

The polymers mentioned display side-effects because their selectivity is too low and their binding of vitamins is too high, and because of interactions with drugs administered at the same time. Furthermore they can modify the composition of bile acid in the bile. These properties manifest themselves in various gastrointestinal disturbances (for example constipation, steatorrhea), avitaminoses and an increased risk of cholelithiasis.

Surprisingly, novel monomeric bile acid derivatives have now been found which can interrupt the enterohepatic circulation of bile acids and do not have the disadvantages mentioned.

The invention therefore relates to monomeric bile acid derivatives of the formula I $$Z-X-GS \qquad I,$$

in which
  GS is a bile acid radical having an acid function in the side chain or a salt thereof,
  X is a covalent bond or a bridge group of the formula $(CH_2)_n$, where n=1 to 10, in which the alkylene chain can contain 1 to 3 oxygen atoms, NH or

groups, and in which GS is bonded via X as desired, and

Z is

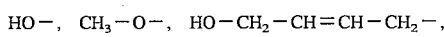

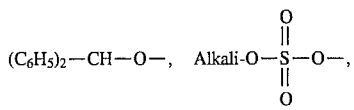

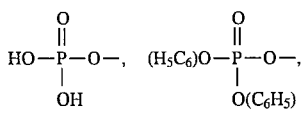

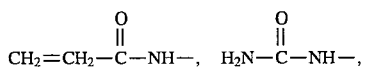

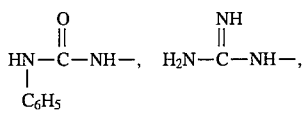

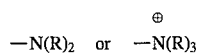

where R is in each case $C_1$-$C_7$ alkyl, or $H_2$—N—$(CH_2)_{6-}$,

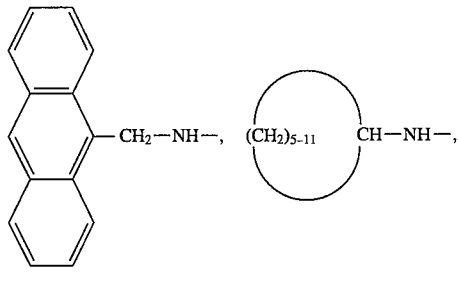

where the alkyl moiety is optionally substituted by a COOH group,

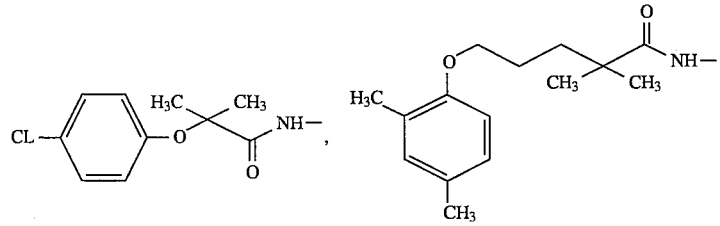

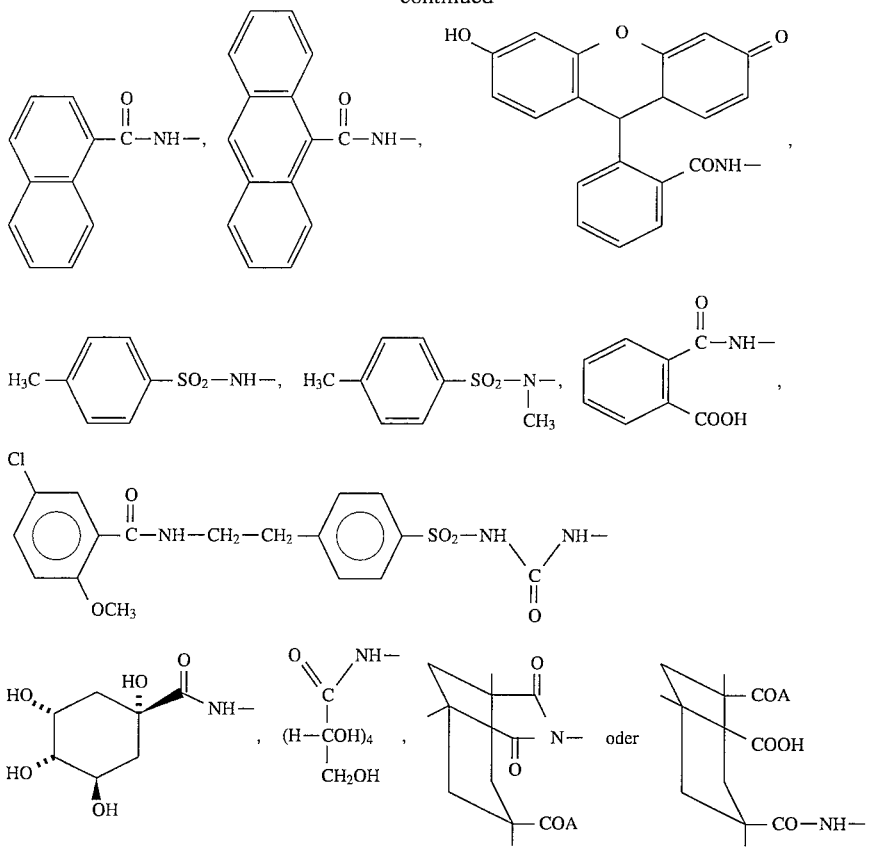

where A is in each case OH or $NH(C_1-C_{10})$alkyl.

Preferred compounds of the formula I are those in which GS is linked to X in the 3-position, linking taking place in the α- or β-position.

An acid function is understood as meaning, in particular, the COOH group or the sulfonic acid group.

Alkyl radicals are straight-chain or branched.

The compounds of the formula (I) according to the invention have a high affinity for the specific bile acid transportation system of the small intestine and inhibit bile acid absorption in a concentration-dependent and competitive manner.

By competitive inhibition, intervention in the enterohepatic circulation can be considerably more selective. Avitaminoses are not to be expected, and a qualitative change in the bile acid composition in the bile is just as unlikely. A controlled reduction in the serum cholesterol level can be achieved with compounds according to the invention, without the known side effects being observed. Because of their high affinity for the bile acid transportation system, very much lower daily doses than with the commercially available polymers are sufficient; this also leads to a high acceptance by patient and doctor.

The compounds have valuable pharmacological properties and are therefore particularly suitable as hypolipidemic agents.

The invention thus also relates to medicaments based on the compounds of the formula (I) and to the use of the compounds as medicaments, in particular for reducing the cholesterol level.

The compounds according to the invention were tested biologically by determination of the inhibition of [$^3$H] taurocholate uptake in the brush border membrane vesicles from the ileum of rabbits. The inhibition test was carried out as follows:

1. Preparation of brush border membrane vesicles from the ileum of rabbits

Brush border membrane vesicles were prepared from the intestinal cells of the small intestine by the so-called $Mg^{2+}$ precipitation method. Male New Zealand rabbits (2 to 2.5 kg body weight) were sacrificed by intravenous injection of 0.5 ml of an aqueous solution of 2.5 mg of tetracaine HCl, 100 T 61$^R$ and 25 mg of mebezonium iodide. The small intestine was removed and rinsed with ice-cold physiological saline solution. The terminal 7/10 of the small intestine (measured in the oral-rectal direction, i.e. the terminal ileum, which contains the active $Na^+$-dependent bile acid transportation system) was used for preparation of the brush border membrane vesicle. The intestines were frozen in plastic bags under nitrogen at −80° C. For preparation of the membrane vesicles, the frozen intestines were thawed at 30° C. in a water bath. The mucosa was scraped off and suspended in 60 ml of ice-cold 12 mM Tris/HCl buffer (pH 7.1)/300 mM mannitol, 5 mM EGTA/10 mg/l of phenylmethylsulfonyl fluoride/1 mg/l of trypsin inhibitor from soybeans (32 U/mg)/0.5 mg/l of trypsin inhibitor from bovine lung (193 U/mg)/5 mg/l of bacitracin. After dilution to 300 ml with ice-cold distilled water, the mixture was homogenized with an Ultraturrax (18-rod, IKA Werk Staufen, FRG) for 3 minutes at 75% of the maximum output, while cooling with ice. After addition of 3 ml of 1M $MgCl_2$ solution (final concentration 10 mM), the mixture was left to stand at 0° C. for exactly 1 minute. The cell membranes aggregate by addition of $Mg^{2+}$ and precipitate, with the exception of the brush border membranes. After centrifugation at 3000× g (5000 rpm, SS-34 rotor) for 15 minutes, the precipitate was discarded, and the supernatant, which contained the brush border membranes, was centrifuged at 267000× g (15000 rpm, SS-34 rotor) for 30 minutes. The supernatant was discarded and the precipitate was rehomogenized in 60 ml of 12 mM Tris/HCl buffer (pH 7.1)/60 mM mannitol, 5 mM EGTA using a Potter Elvejhem homogenizer (Braun, Melsungen, 900 rpm, 10 strokes). After addition of 0.1 ml of 1 M $MgCl_2$ solution and an incubation time of 15 minutes at 0° C., the mixture was centrifuged again at 3000× g for 15 minutes. The supernatant was then centrifuged again at 46000× g (15000 rpm, SS-34 rotor) for 30 minutes. The precipitate was taken up in 30 ml of 10 mM Tris/Hepes buffer (pH 7.4)/300 mM mannitol and resuspended homogeneously by 20 strokes in a Potter Elvejhem homogenizer at 1000 rpm. After centrifugation at 48000× g (20000 rpm, SS-34 rotor) for 30 minutes, the precipitate was taken up in 0.5 to 2 ml of Tris/Hepes buffer (pH 7.4)/280 mM mannitol (final concentration 20 mg/ml) and resuspended with the aid of a tuberculin syringe with a 27 gauge needle. The vesicles were either used immediately for transportation studies after preparation, or stored at −196° C. in portions of 4 mg in liquid nitrogen.

2. Inhibition of $Na^+$-dependent [$^3$H]-taurocholate uptake in the brush border membrane vesicles of the ileum The uptake of substrates into the brush border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the corresponding ligands (90 μl). The incubation medium contained 0.75 μl=0.75 μCi of [$^3$H(G)]-taurocholate (specific activity: 2.1 Ci/mmol)/0.5 μl of 10 mM taurocholate/8.75 μl of sodium transportation buffer (10 mM Tris/Hepes (pH 7.4)/100 mM mannitol/100 mM NaCl) (Na—T—P) or 8.75 μl of potassium transportation buffer (10 mM Tris/Hepes (pH 7.4)/100 mM mannitol/100 mM KCl) (K—T—P) and 80 μl of the inhibitor solution in question, dissolved in Na-T buffer or K-T buffer, depending on the experiment. The incubation medium was filtered through a polyvinylidene fluoride membrane filter (SYHV LO 4NS, 0.45 μm, 4 mm φ, Millipore, Eschborn, FRG). The transportation measurement was started by mixing the vesicles with the incubation medium. The concentration of taurocholate in the incubation batch was 50 μM. After the desired incubation time (usually 1 minute), the transportation was stopped by addition of 1 ml of ice-cold stopping solution (10 mM Tris/Hepes (pH 7.4)/150 mM KCl).

The mixture formed was immediately filtered off with suction over a membrane filter of cellulose nitrate (ME 25, 0.45 μm, 25 mm diameter, Schleicher & Schuell, Dassell, FRG) under a vacuum of 25 to 35 mbar. The filter was rinsed with 5 ml of ice-cold stopping solution.

To measure the uptake of the radioactively labeled taurocholate, the membrane filter was dissolved with 4 ml of the scintillator Quickszint 361 (Zinsser Analytik GmbH, Frankfurt, FRG) and the radioactivity was measured by liquid scintillation measurement in a TriCarb 2500 measuring instrument (Canberra Packard GmbH, Frankfurt, FRG). After calibration of the instrument with the aid of standard samples and after correction for any chemiluminescence present, the values measured were obtained as dpm (decompositions per minute).

The control values were in each case determined in Na—T—P and K—T—P. The difference between the uptake in Na—T—P and K—T—P was the $Na^+$-dependent transportation content. The concentration of inhibitor at which the $Na^+$-dependent transportation content was inhibited by 50%—based on the control—was designated as the $IC_{50}Na^+$.

The table shows the measurement values of the inhibition of the [$^3$H]-taurocholate uptake in brush border membrane vesicles from the ileum of rabbits. The quotients of the $IC_{50}$ and $IC_{50Na}$ values of the taurochenodesoxycholate (TCDC) investigated as the standard in each vesicle preparation and the particular substance are stated.

| Substance from Example: | $\dfrac{IC_{50} \text{ (TCDC)}}{IC_{50} \text{ (Substance)}}$ | $\dfrac{IC_{50Na} \text{ (TCDC)}}{IC_{50Na} \text{ (Substance)}}$ |
|---|---|---|
| 3 | 0.4 | 0.35 |
| 4 | 0.77 | 0.69 |
| 18 | 0.47 | 0.42 |
| 21 | 0.34 | 0.33 |
| 33 | 0.33 | 0.35 |
| 35 | 1.0 | 1.02 |
| 36 | 0.19 | 0.20 |
| 38 | 0.49 | 0.41 |
| 40 | 0.52 | 0.50 |
| 43 | 0.78 | 0.73 |

The invention furthermore relates to the use of the compounds according to the invention for the preparation of a medicine.

For this, the compounds of the formula I are dissolved or suspended in pharmacologically acceptable organic solvents, such as mono- or polyhydric alcohols, such as, for example, ethanol or glycerol, or in triacetin, oils, for example sunflower oil or cod-liver oil, ethers, such as, for example, diethylene glycol dimethyl ether, or also polyethers, for example polyethylene glycol, or also in the presence of other pharmacologically acceptable polymeric carriers, such as, for example, polyvinylpyrrolidone, or other pharmaceutically acceptable additives, such as starch, cyclodextrin or polysaccharides. The compounds according to the invention furthermore can be administered in combination with other medicaments.

The compounds of the formula I are administered in various dosage forms, preferably orally in the form of tablets, capsules or liquids. The daily dose varies in the range from 3 mg to 5000 mg, but preferably in the dose range of 10 to 1000 mg, depending on the body weight and constitution of the patient.

The particular monoisotopic molecular weights calculated are stated in the following examples.

Unless stated otherwise, mass spectra were recorded by the FAB technique with addition of LiCl and 3-nitrobenzaldehyde[3-NBA].

Starting compounds which have the bile acid structure have already been described in some cases (cf., for example, EP-A-0 417 725, EP-A-0 489 423 and EP-A-0 548 793.

$R^1$ is defined in Example 6.

EXAMPLE 1

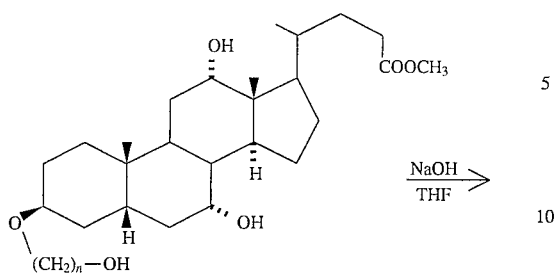

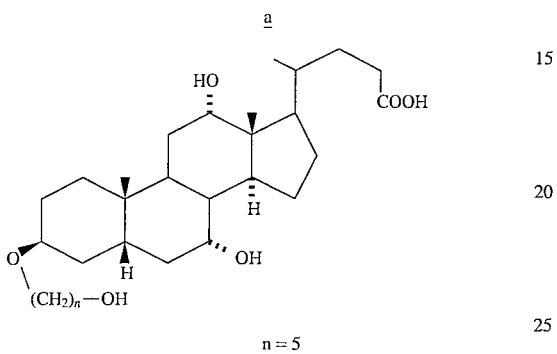

n = 5

1 g (1.96 mmol) of the methyl ester a is dissolved in 15 ml of tetrahydrofuran (THF) or 1,4-dioxane and the solution is stirred intensively with 10 ml of 2N NaOH overnight at room temperature. It is then diluted with a large quantity of water and acidified with half-concentrated hydrochloric acid, while cooling with ice. Precipitation is brought to completion by subsequent stirring for 1 hour, while cooling with ice, and the precipitate formed is filtered off with suction and rinsed with cold water. Recrystallization from ethanol/water and drying in vacuo give 940 mg (96%) of Example 1.

$C_{29}H_{50}O_6$ (494) MS: 501 (M+Li$^+$).

The following Examples 2 to 7 are prepared analogously to "Example 1" from the corresponding bile acid esters:

| Example No. | as "Example 1" where n = | Empirical formula | MW | MS |
|---|---|---|---|---|
| 2 | 6 | $C_{30}H_{52}O_6$ | 508 | 515 (M + Li$^+$) |
| 3 | 8 | $C_{32}H_{56}O_6$ | 536 | 543 (M + Li$^+$) |
| 4 | 9 | $C_{33}H_{58}O_6$ | 550 | 557 (M + Li$^+$) |
| 5 | 10 | $C_{34}H_{60}O_6$ | 564 | 571 (M + Li$^+$) |

EXAMPLE 6

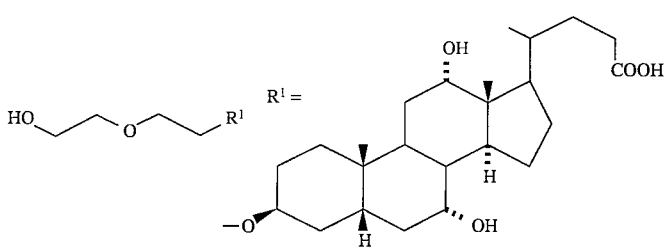

$C_{28}H_{48}O_7$ (496)  MS: 503 (M + Li$^+$)

EXAMPLE 7

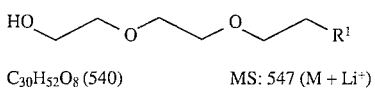

$C_{30}H_{52}O_8$ (540)  MS: 547 (M + Li$^+$)

EXAMPLE 8

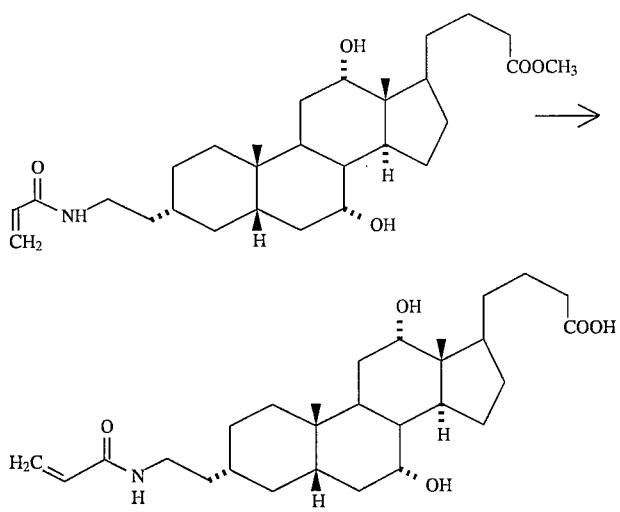

100 mg (0.2 mmol) of the methyl ester are dissolved in 10 ml of dioxane and the solution is stirred with 3 ml of half-concentrated sodium hydroxide solution at room temperature for 6 hours. The mixture is diluted with water and acidified with half-concentrated hydrochloric acid to give, after filtration with suction and washing, the acid "Example 8" (50 mg, 51%).

$C_{29}H_{47}NO_5$ (489) MS: 496 (M+Li$^+$)

The following substance examples were prepared as for "Example 8":

EXAMPLE 9

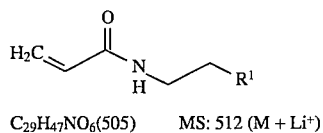

$C_{29}H_{47}NO_6$ (505)   MS: 512 (M + Li$^+$)

EXAMPLE 10

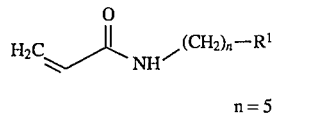

n = 5

$C_{32}H_{53}NO_6$ (547)   MS: 554 (M + Li$^+$)

EXAMPLE 11

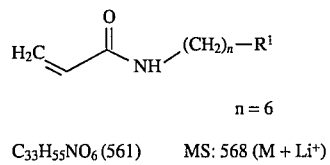

n = 6

$C_{33}H_{55}NO_6$ (561)   MS: 568 (M + Li$^+$)

EXAMPLE 12

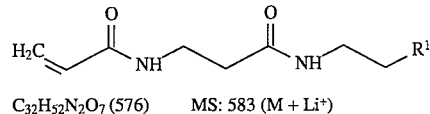

$C_{32}H_{52}N_2O_7$ (576)   MS: 583 (M + Li$^+$)

EXAMPLE 13

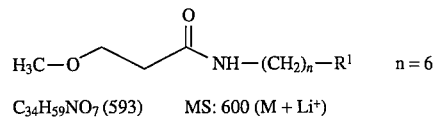   n = 6

$C_{34}H_{59}NO_7$ (593)   MS: 600 (M + Li$^+$)

EXAMPLE 14

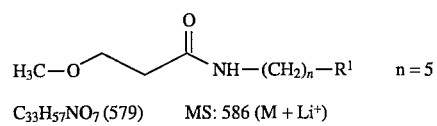   n = 5

$C_{33}H_{57}NO_7$ (579)   MS: 586 (M + Li$^+$)

EXAMPLE 15

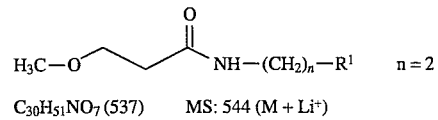   n = 2

$C_{30}H_{51}NO_7$ (537)   MS: 544 (M + Li$^+$)

EXAMPLE 16

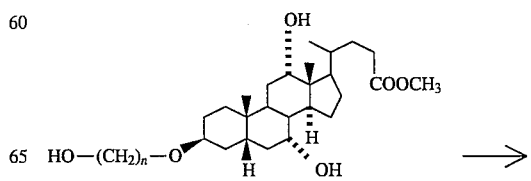

-continued

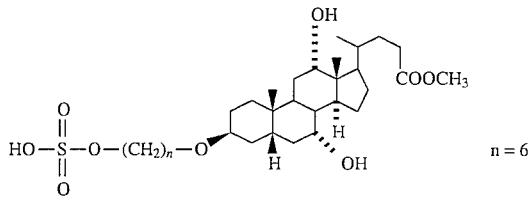
n = 6

0.84 ml of triethylamine is added to 3.14 g (6 mmol) of the primary alcohol a (n =6) in 100 ml of dry methylene chloride and the mixture is cooled to −10° C. 0.4 ml (6 mmol) of chlorosulfonic acid in 20 ml of dry methylene chloride is added to the solution at this temperature. After 1 hour at 0° C. and 1 hour at room temperature, water is added, the organic phase is separated off, the aqueous phase is extracted several times with ethyl acetate and the combined organic phases are dried and concentrated. The residue is purified by chromatography ($SiO_2$, ethyl acetate/methanol=3:1). 1.45 g (40%) of "Example 16" are obtained.

$C_{31}H_{54}O_9S$ (602) MS: 631 (M–$H^+$+$Li^+$+$Na^+$) 615 (M–$H^+$ 2$Li^+$)

EXAMPLE 17

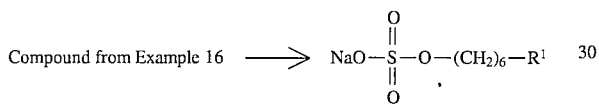

0.5 g (0.83 mmol) of "Example 16" is stirred in 20 ml of dioxane with 7 ml of half-concentrated sodium hydroxide solution at room temperature for 6 hours. The mixture is then acidified with half-concentrated hydrochloric acid, while cooling, and is concentrated in vacuo. The residue is purified by column filtration ($SiO_2$, ethyl acetate/methanol=3:1). 254 mg (52%) of "Example 17" are obtained.

$C_{30}H_{51}O_9S$ (610) MS=617 (M+$Li^+$) 601 (M–$Na^+$+2$Li^+$)

EXAMPLE 18

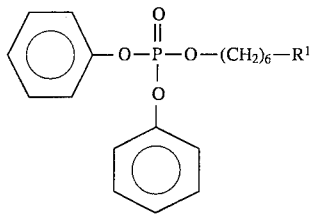

15 ml of phosphoric acid diphenyl ester chloride are added dropwise to a solution of 2.6 g (5.12 mmol) of "Example 2" in 20 ml of pyridine at 0 to 5° C. and the mixture is subsequently stirred at room temperature for 2 hours. It is poured onto 200 ml of ice-water, about 15 ml of concentrated sulfuric acid are added, while stirring and cooling, and the mixture is extracted several times with ethyl acetate. The organic phase is dried and concentrated and the residue is purified by chromatography ($SiO_2$, $CH_2Cl_2$/$CH_3OH$=10:1). 1.78 g (47%) of "Example 18" are obtained.

$C_{42}H_{61}O_9P$ (740) MS: 747 (M+$Li^+$)

EXAMPLE 19

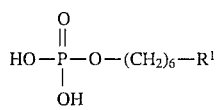

1 g (1.35 mmol) of "Example 18" is hydrogenated in 50 ml of glacial acetic acid with a spatula-tip of platinum-on-charcoal in a shaking vessel. When the reaction has ended (about 4 hours), the catalyst is filtered off with suction and the filtrate is concentrated. The residue is purified by column filtration ($SiO_2$, ethyl acetate/$CH_3OH$=2:1). 270 mg (34%) of "Example 19" are obtained.

$C_{30}H_{53}O_9P$ (588) MS: 601 (M–$H^+$+2$Li^+$) 595 (M+$Li^+$)

EXAMPLE 20

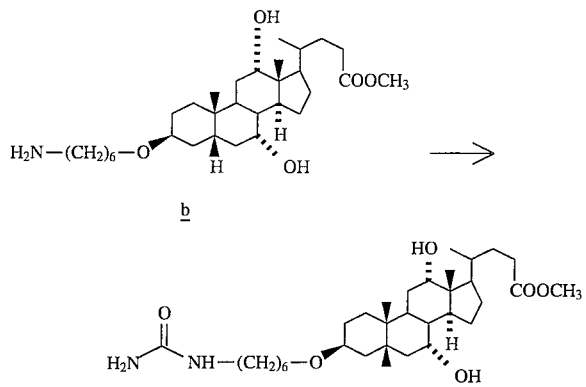

2.24 g (4 mmol) of amine h and 324 mg (4 mmol) of potassium cyanate are suspended in 60 ml of water and the suspension is heated to boiling point. A solution is formed, from which a solid precipitates after a short time. The mixture is stirred at boiling point for 30 minutes and cooled, about 40 ml of water are added and the mixture is acidified with dilute hydrochloric acid. It is extracted several times with ethyl acetate, the organic phase is dried and concentrated in vacuo and the residue is purified by chromatography ($SiO_2$, EtOAc/$CH_3OH$=10:1). 520 mg (23%) of "Example 20" are obtained.

$C_{32}H_{56}N_2O_6$ (564) MS: 571 (M+$Li^+$)

EXAMPLE 21

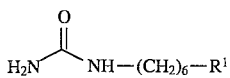

450 mg (0.mmol) of "Example 20" are stirred in 10 ml of dioxane with 5 ml of half-concentrated sodium hydroxide solution at room temperature for 6 hours. When the reaction has ended, the mixture is diluted with water, acidified with hydrochloric acid and subsequently stirred in an ice-bath for 1 hour. The precipitate is filtered off with suction and rinsed with water to give, after drying in vacuo, 430 mg (97%) of "Example 21".

$C_{31}H_{54}N_2O_6$ (550) MS: 557 (M+$Li^+$)

EXAMPLE 22

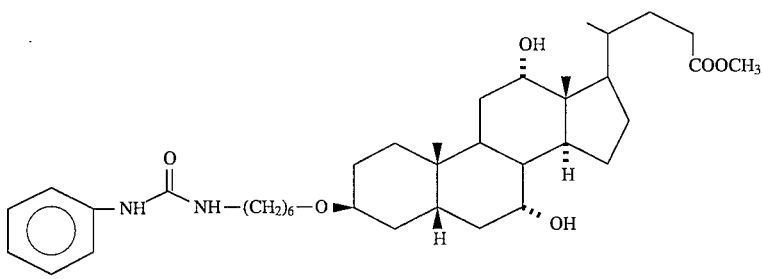

2 mmol of phenyl isocyanate in 5 ml of methylene chloride are added to 1.04 g (2 mmol) of amine b (Example 20) in 50 ml of dry methylene chloride and 28 ml of triethylamine at 0° C. The mixture is subsequently stirred at room temperature for 6 hours and worked up as described under "Example 16", the aqueous phase being acidified. After column filtration ($CH_2Cl_2/CH_3OH=10:1$), 6540 mg (51%) of "Example 22" are obtained.

$C_{38}H_{60}N_2O_6$ (640) MS: 647 (M+Li$^+$)

EXAMPLE 23

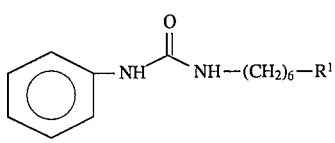

$C_{37}H_{58}N_2O_6$ MS: 633 (M+Li$^+$)

EXAMPLE 24

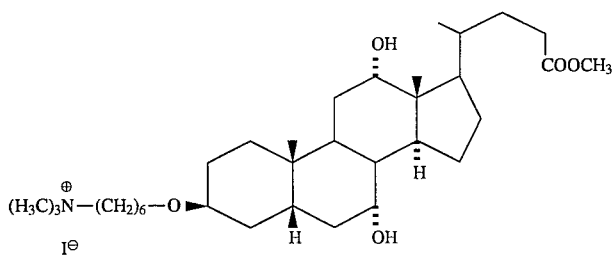

2.08 g (4 mmol) of amine b, 10 ml of triisobutylamine and 5 ml of iodomethane are heated at boiling point in 50 ml of acetonitrile for 2 hours. All the volatile constituents are removed in vacuo and the residue is purified by chromatography ($SiO_2$, $CH_2Cl_2/CH_3OH=10:1$). 1.2 g (43%) of "Example 24" are obtained.

$C_{34}H_{62}INO_5$ (691) MS (FAB, 3-NBA): 564 (M–I$^\ominus$)

EXAMPLE 25

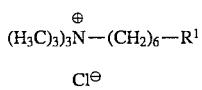

Compound Example 25 is prepared from Example 24 analogously to "Example 21". The crude product is purified by medium pressure chromatography over RP-8 silica gel ($CH_3OH/H_2O=7:3$).

$C_{33}H_{60}ClNO_5$ (585) MS (FAB, 3-NBA): 550 (M–Cl$^\ominus$)

EXAMPLE 26

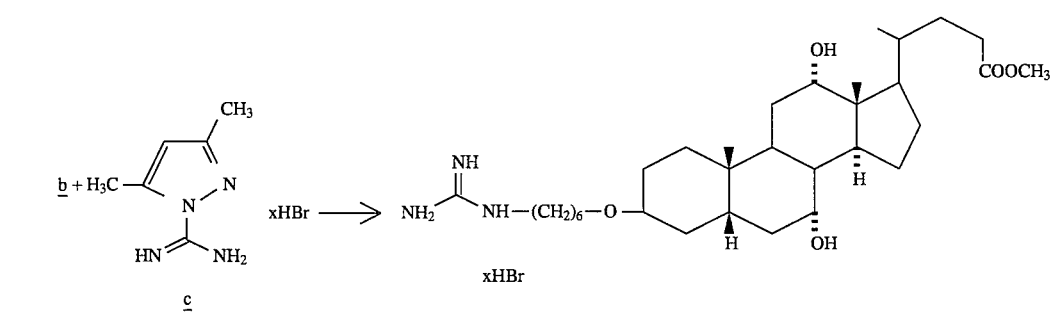

1.04 g (2 mmol) of amine b and 276 mg (2 mmol) of pyrazole c are heated under reflux in 40 ml of dry acetonitrile for 10 hours. After cooling and addition of ether, a precipitate is formed, and is filtered off with suction and rinsed with dry ether. After drying, 450 mg of "Example 26" are obtained.

$C_{32}H_{58}BrN_3O_5$ (643) MS: 570 (M–HBr+Li$^+$) 564 (M–Br$^\ominus$)

EXAMPLE 27

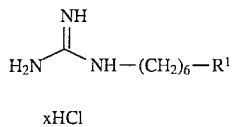

xHCl is prepared analogously to "Example 21".
$C_{31}H_{56}ClN_3O_5$ (585) MS: 556 (M–HCl+Li$^+$) 550 (M–Cl$^\ominus$)

EXAMPLE 28

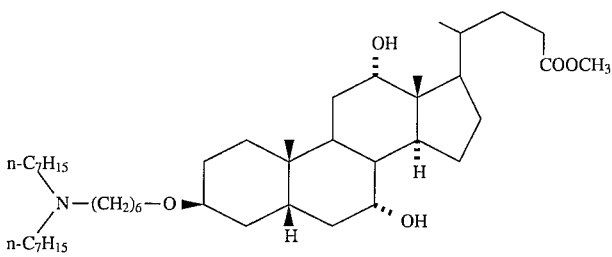

1.0 g (1.9 mmol) of amine b, 265 mg of NaBH$_3$CN and 610 mg of heptanal are stirred in 10 ml of dry methanol at room temperature for 48 hours. The mixture is concentrated in vacuo, the residue is partitioned between ethyl acetate and saturated bicarbonate solution and the residue of the organic phase is purified by chromatography. In addition to a small amount of monoheptylamino derivative, 650 mg (49%) of "Example 28" are obtained.

$C_{45}H_{83}NO_5$ (718) MS: 725 (M+Li$^+$)

EXAMPLE 29

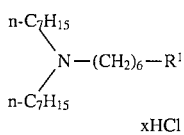

xHCl is prepared analogously to "Example 21". The aqueous phase is decanted off from the oily crude product after acidification, and the residue is extracted by stirring with ethyl acetate and then filtered off with suction and dried.

$C_{44}H_{82}ClNO_5$ (740) MS: 711 (M–HCl+Li$^+$) 705 (M–Cl$^\ominus$)

EXAMPLE 30

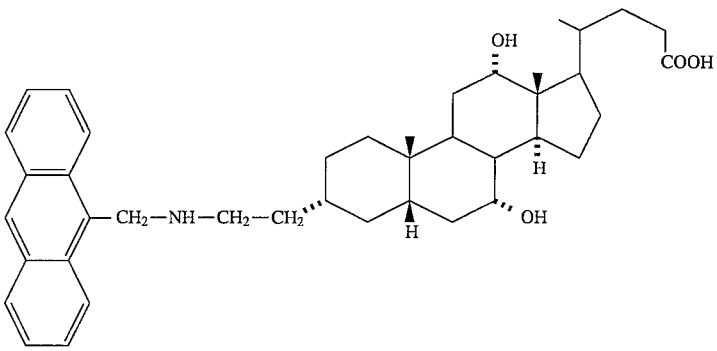

is prepared analogously to "Example 28" and "Example 29" by reductive amination of anthracene-9-carbaldehyde with methyl 3α-(aminoethyl)-7α, 12α-dihydroxy-24-cholanate (d) and subsequent alkaline hydrolysis.

$C_{41}H_{55}NO_4$ (625) MS: 632 (M+Li$^+$)

EXAMPLE 31

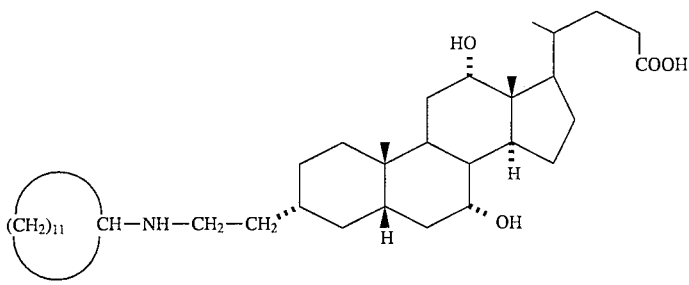

is prepared analogously to "Example 30" using cyclododecanone as the carbonyl component.

$C_{38}H_{87}NO_4$ (602) MS: 609 (M+Li$^+$)

EXAMPLE 32

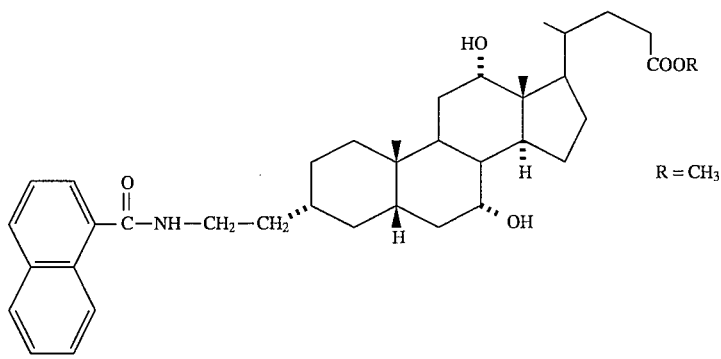

R = CH$_3$ 0.38 g (2 mmol) of naphthoyl chloride in 5 ml of CH$_2$Cl$_2$ is added to 0.9 g (2 mmol) of amine d and 0.6 ml of triethylamine in 20 ml of dry CH$_2$Cl$_2$, while cooling with ice. The mixture is subsequently stirred at 0° C. for 1 hour and left to stand overnight. Water is added, and the mixture is acidified and extracted several times with CH$_2$Cl$_2$. The residue from the organic phase is purified by chromatography (SiO$_2$, EtOAc/cyclohexane=3:1). 1 g (83%) of "Example 32" is obtained.

$C_{38}H_{53}NO_5$ (603) MS: 610 (M+Li$^+$)

EXAMPLE 33

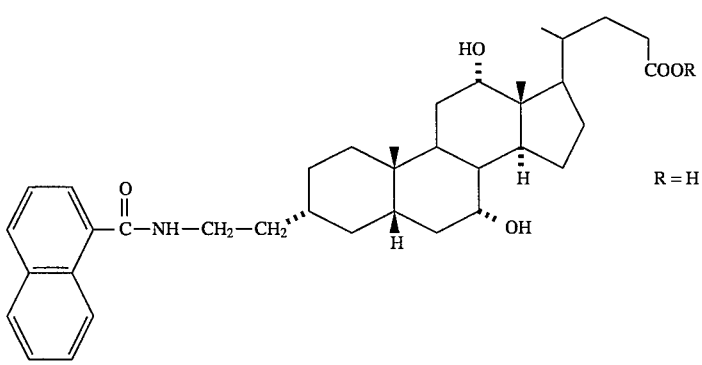

R = H is prepared analogously to "Example 21".

$C_{37}H_{51}NO_5$ (589) MS: 596 (M+Li$^+$)

EXAMPLE 34

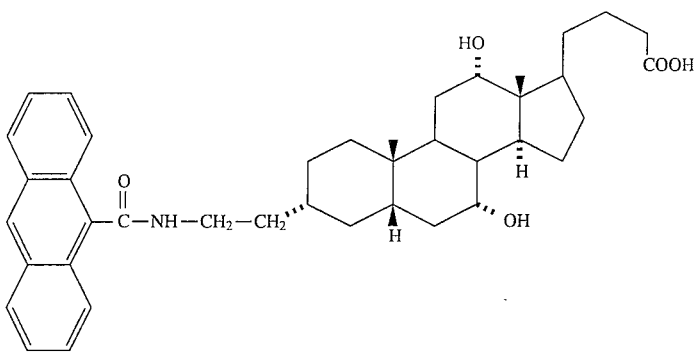

is prepared analogously to "Example 32" and "Example 33" using anthracene-9-carbonyl chloride.

$C_{41}H_{53}NO_5$ (639) MS: 646 (M+Li$^+$)

EXAMPLE 35

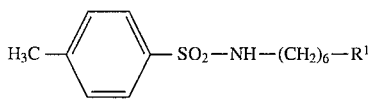

is prepared analogously to "Example 34" using p-toluenesulfonyl chloride and amine b.

$C_{37}H_{59}NO_7S$ (661) MS: 668 (M+Li$^+$)

EXAMPLE 36

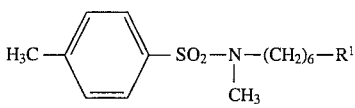

is prepared analogously to "Example 35". The methyl ester obtained as an intermediate product is methylated in dimethylformamide, after deprotonation by sodium hydride, with iodomethane at room temperature. The product is then subjected to alkaline hydrolysis analogously to "Example 35".

$C_{38}H_{61}NO_7S$ (675) MS: 688 (M–H$^+$+2Li$^+$) 682 (M+Li$^+$)

EXAMPLE 37

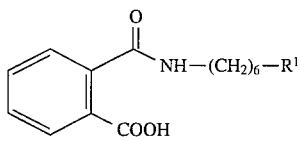

is prepared analogously to "Example 34" using o-phthalic anhydride and amine b.

$C_{38}H_{57}NO_8$ (655) MS: 668 (M–H$^+$+2Li$^+$) 662 M+Li$^+$)

EXAMPLE 38

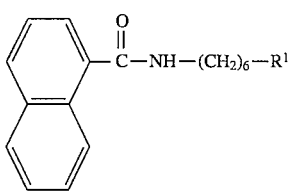

is prepared analogously to "Example 32"/"Example 33" using amine b.

$C_{41}H_{59}NO_6$ (661) MS: 668 (M+Li$^+$)

EXAMPLE 39

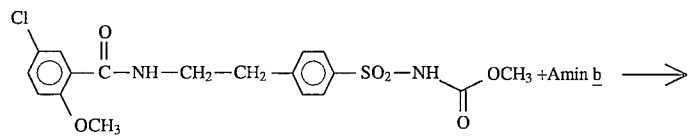

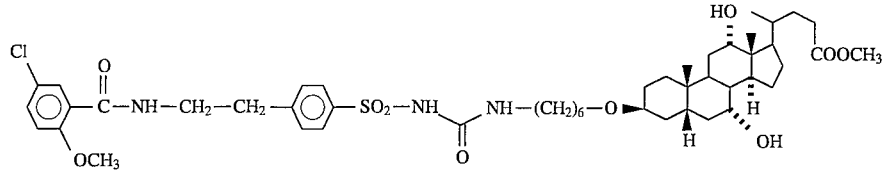

426 mg (1 mmol) of urethane and 782 mg (15 mmol) of amine b are heated under reflux in 50 ml of dioxane for 4 hours. The mixture is then concentrated and the residue is purified by chromatography (SiO$_2$, CH$_2$Cl$_2$/CH$_3$OH=10:1). 540 g (59%) of "Example 39" are obtained.

C$_{48}$H$_{70}$ClN$_3$O$_{10}$S (915) MS: 922 (M+Li$^+$)

EXAMPLE 40

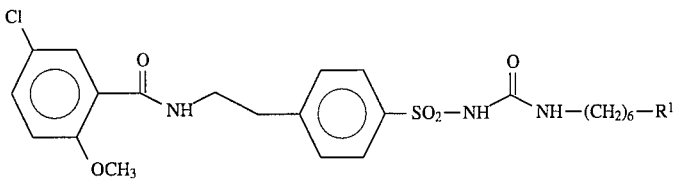

is prepared analogously to "Example 21".

C$_{47}$H$_{68}$ClN$_3$O$_{10}$S (901) MS (electrospray): 902 (M+H$^+$)

EXAMPLE 41

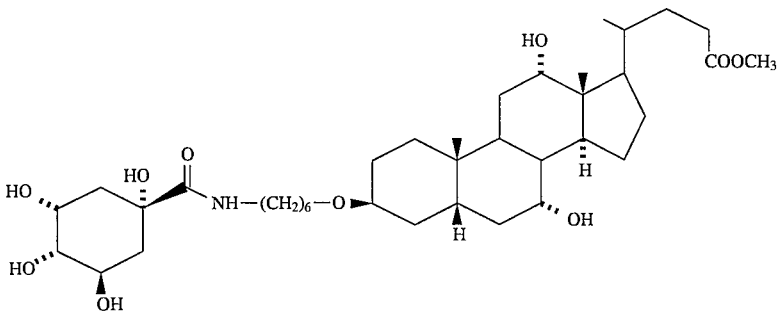

750 mg (3.6 mmol) of dicyclohexylcarbodiimide are added to a solution of 1.56 g (3 mmol) of amine b, 576 mg (3 mmol) of China acid and 490 mg (83.6 mmol) of hydroxybenzotriazole in 100 ml of THF. The mixture is stirred at room temperature for 40 hours. The urea formed is filtered off, the solution is concentrated and the residue is taken up in ethyl acetate. The solution is washed with saturated NaHCO$_3$ solution, 2N citric acid, saturated NaHCO$_3$ solution and water. The residue from the organic phase is purified by chromatography (SiO$_2$, ethyl acetate/CH$_3$OH= 5:1). 1.2 g (58%) of "Example 41" are obtained.

C$_{38}$H$_{65}$NO$_{10}$ (695) MS: 702 (M+Li$^+$)

EXAMPLE 42

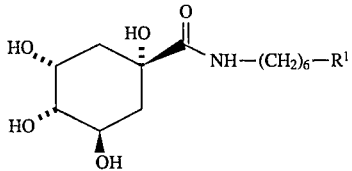

is prepared analogously to "Example 21".

C$_{37}$H$_{63}$NO$_{10}$ (681) MS (FAB, 3-NBA): 682 (M+H$^+$)

EXAMPLE 43

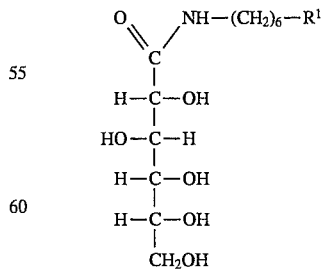

is prepared analogously to "Example 41"/"Example 42" using gluconic acid.

C$_{36}$H$_{63}$NO$_{11}$ (685) MS: 714 (M–H$^+$+Li$^+$+Na$^+$)

EXAMPLE 44

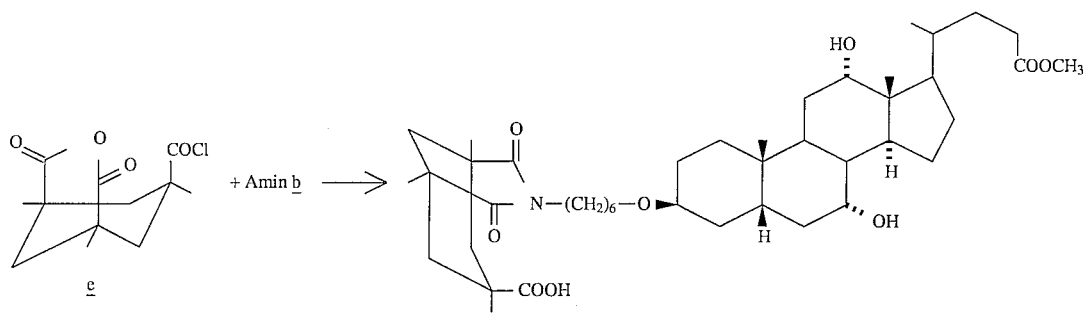

1.04 g (4 mmol) of acid chloride e, 2.1 g (4 mmol) of amine b and a spatula-tip of 4-dimethylaminopyridine are stirred in 40 ml of dry pyridine at room temperature for 6 hours. After standing overnight at room temperature, the mixture is concentrated in vacuo. "Example 44" is isolated after purification by chromatography ($SiO_2$, $CH_2Cl_2/CH_3OH=20:1$).

$C_{43}H_{69}NO_9$ (743) MS: 750 (M+Li$^+$)

EXAMPLE 45

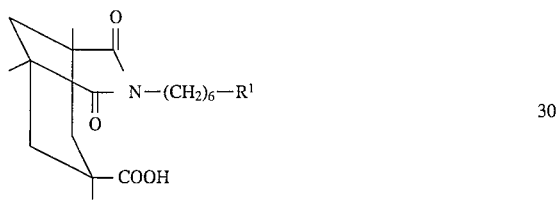

is prepared analogously to "Example 21".

$C_{42}H_{67}NO_9$ (729) MS: 742 (M–H$^+$+2Li$^+$) 736 (M+Li$^+$)

EXAMPLE 46

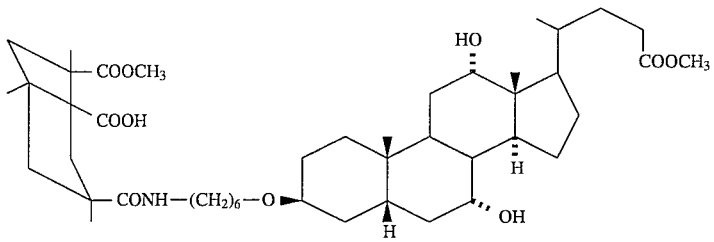

2.6 g (5 mmol) of amine b in $CH_2Cl_2$ are added to 1.3 g (5 mmol) of acid chloride e and 0.8 ml of triethylamine in 50 ml of dry $CH_2Cl_2$, while cooling with ice, and the mixture is stirred at 0° C. for 1 hour. An excess of methanol is then added, the mixture is allowed to come to room temperature, water is added and the mixture is acidified with dilute hydrochloric acid. The aqueous phase is extracted several times by shaking with $CH_2Cl_2$. After purification of the residue from the organic phase by chromatography ($SiO_2$, $CH_2Cl_2/CH_3OH=10:1$), "Example 46" is obtained.

$C_{44}H_{73}NO_{10}$ (775) MS: 783 (M+Li$^+$)

EXAMPLE 47

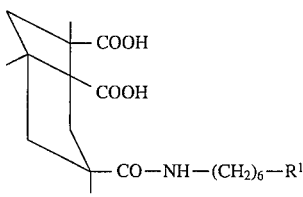

is prepared analogously to "Example 21".

$C_{42}H_{69}NO_{10}$ (747) MS: 760 (M–H$^+$+2Li$^+$) 754 ((M+Li$^+$)

EXAMPLE 48

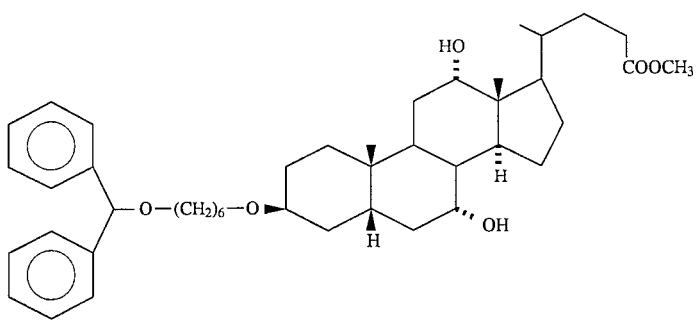

3.14 g (6 mmol) of alcohol a (n=6) are heated at 100° C. with 3 ml of ethyldiisopropylamine and 1.5 g of diphenylmethyl bromide in 50 ml of DMF for 8 hours. After aqueous working up and purification by chromatography (SiO$_2$, CH$_2$Cl$_2$/CH$_3$OH=10:1), "Example 48" is obtained.

$C_{44}H_{64}O_6$ (688) MS: 695 (M+Li$^+$)

EXAMPLE 49

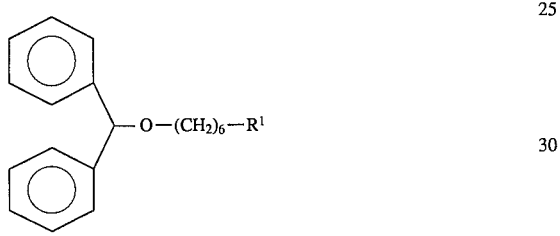

is prepared analogously to "Example 21".

$C_{43}H_{62}O_6$ (674) MS: 681 (M+Li$^+$)

The following compounds are prepared analogously to Example 1 from the corresponding bile acid esters by alkaline ester hydrolysis:

EXAMPLE 50

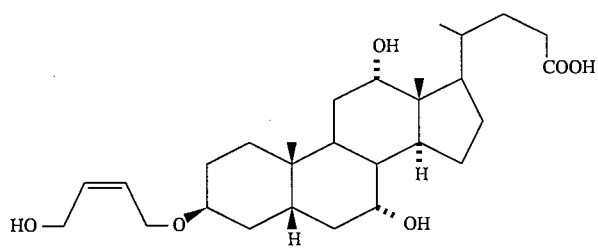

$C_{28}H_{46}O_6$ MW: 478 MS: 485 (M+Li$^+$)

EXAMPLE 51

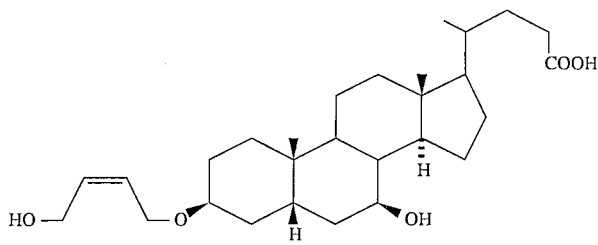

$C_{28}H_{46}O_5$ MW: 462 MS: 469 (M+Li⁺)

EXAMPLE 52

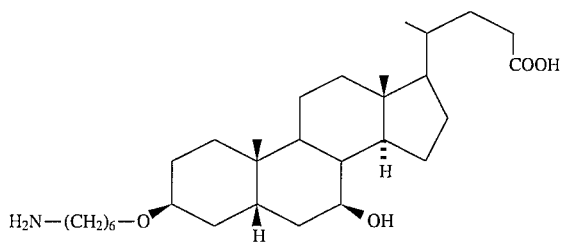

$C_{30}H_{53}NO_{44}$ MW: 491 MS: 498 (M+H⁺)

EXAMPLE 53

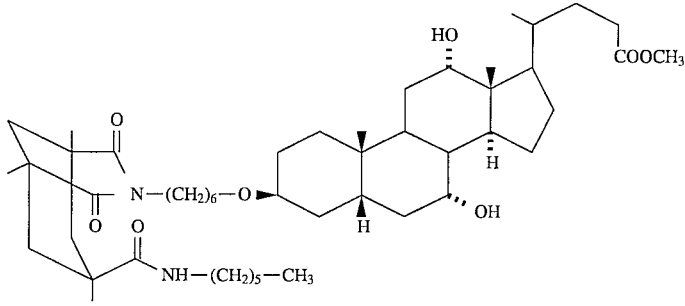

is prepared from Example 44 and n-hexylamine analogously to Example 41 with a reaction time of 25 hours.
$C_{49}H_{82}N_2O_8$ (827) MS: 834 (M+Li⁺)

EXAMPLE 54

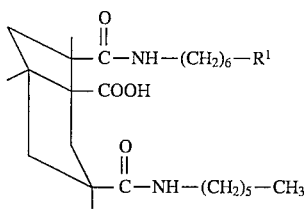

170 mg of "Example 53" are dissolved in 5 ml of dioxane, 1.5 ml of half-concentrated sodium hydroxide and 25 ml of water are added, and the mixture is stirred at room temperature for 12 hours.

A suspended solid is filtered off and the filtrate is acidified with dilute hydrochloric acid, stirring is continued for 1 hour, and the precipitate formed is filtered off with suction. After drying, 154 mg of "Example 54" are obtained.
$C_{48}H_{82}N_2O_9$ (831) MS: 838 (M+Li⁺)

EXAMPLE 55

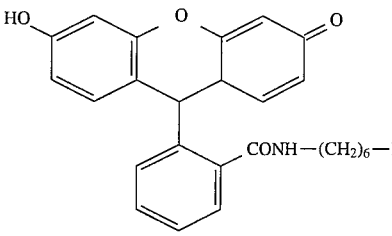

Prepared analogously to "Example 53" and "Example 54" from fluoresceine and amine b.
$C_{50}H_{63}NO_9$ (821) MS: 828 (M+Li⁺)

EXAMPLE 56

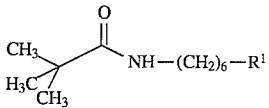

Prepared analogously to "Example 55" from pivalic acid and amine b.
$C_{35}H_{61}NO_6$ (591) MS: 598 (M+Li⁺)

EXAMPLE 57

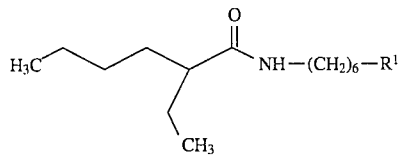

is prepared analogously to "Example 55" from 2-ethylhexanoic acid and amine b.

$C_{38}H_{67}NO_6$ (633) MS: 640 (M+Li$^+$)

EXAMPLE 58

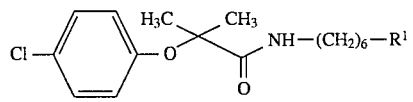

is prepared analogously to "Example 55" from clofibric acid and amine b.

$C_{40}H_{62}ClNO_7$ (703) MS: 710 (M+Li$^+$)

EXAMPLE 59

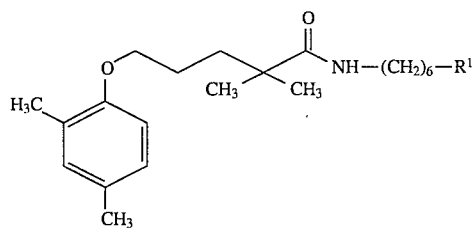

is prepared analogously to "Example 55" from gemfibrocil and amine b.

$C_{45}H_{73}NO_7$ (740) MS: 747 (M+Li$^+$)

EXAMPLE 60

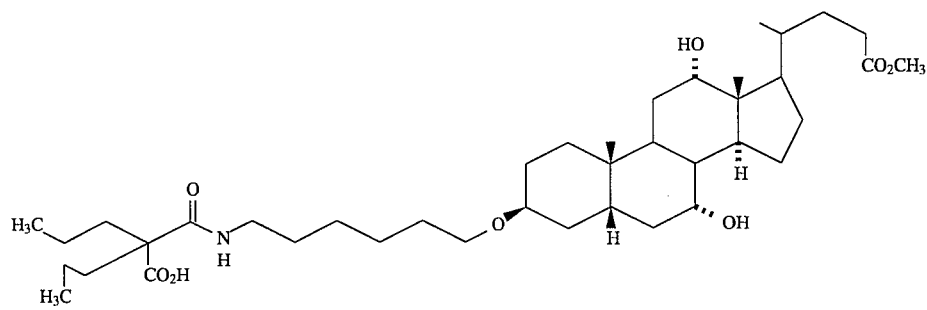

Prepared from 522 mg of amine b and 94.1 mg of di-n-propylmalonic acid in THF in the presence of DCC/HOBT. Isolated after 54 h. The yield is 69%.

$C_{40}H_{69}NO_8$ (690) MS: 697 (M+Li$^+$)

EXAMPLE 61

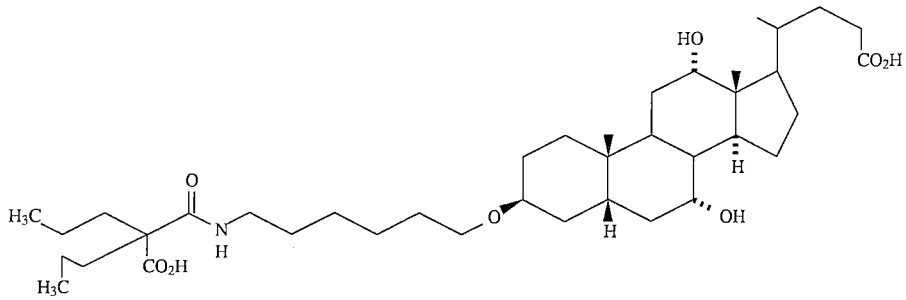

250 mg of "Example 60" are hydrolyzed in dioxane using 2N NaOH. After aqueous work-up and purification by column chromatography (EtOAc/CH$_3$OH 10:1), 160 mg of compound 61 are obtained.

C$_{39}$H$_{67}$NO$_8$ (676) MS: 677 (M+1)

We claim:

1. A monomeric bile acid derivative of the formula IA

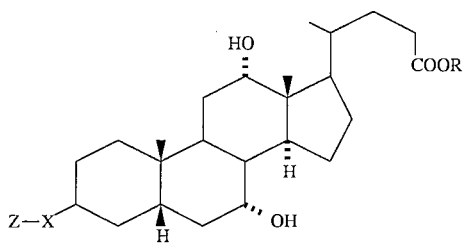

wherein

R is H, CH$_3$ or M and M is a metal capable of forming a salt,

X is a bridge group of the formula (CH$_2$)$_n$, where n=1 to 3, in which 1 to 3 (CH$_2$)-groups can be replaced by NH or

groups, or a bridge group of the formula (CH$_2$)$_n$ where n=4 to 10, in which 1 to 3 (CH$_2$)-groups can be replaced by oxygen atoms, NH or

groups with the proviso that no neighboring (CH$_2$)-groups are replaced by oxygen atoms and in which GS is bonded via X as desired; and Z is

HO—, CH$_3$—O—, HO—CH$_2$—CH=CH—CH$_2$—,

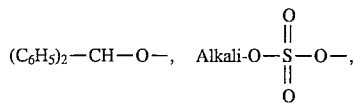

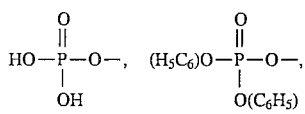

-continued

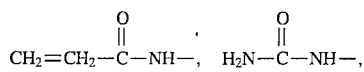

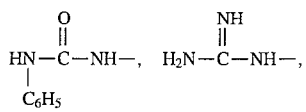

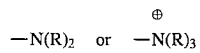

or —N(R)$_3$ where

R is in each case C$_1$-C$_7$ alkyl, or H$_2$—N—(CH$_2$)$_6$;

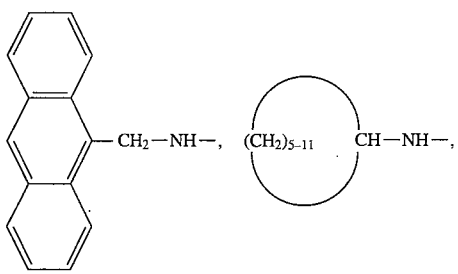

where the alkyl moiety is optionally substituted by a COOH group,

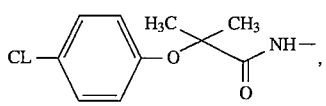

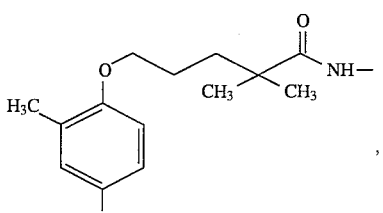

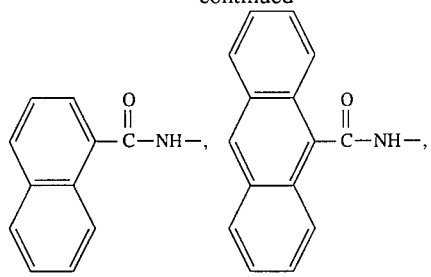
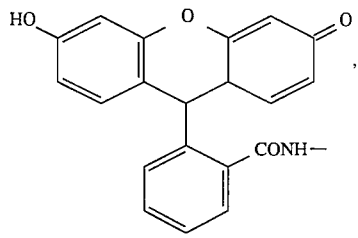
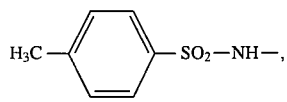
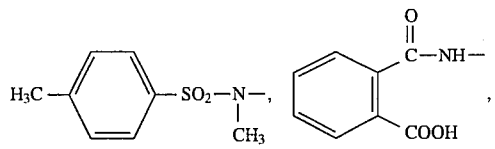
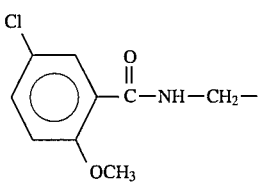
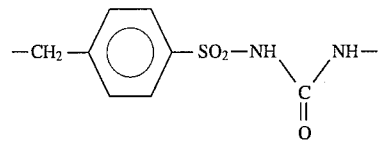
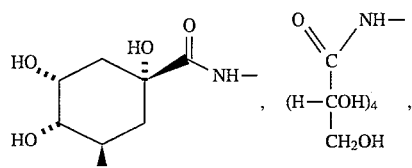
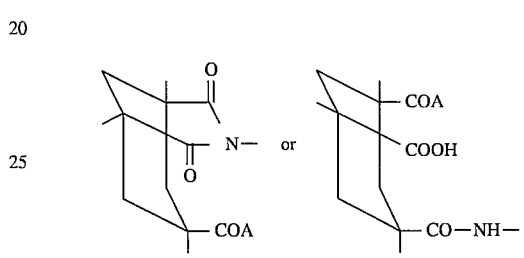
where A is in each case OH or NH $(C_1-C_{10})$ alkyl.
2. A bile acid derivative of the formula I as claimed in claim 1, in which GS is linked to X in the 3-position, linking taking place in the α- or β-position.
3. A medicament comprising a bile acid derivative as claimed in claim 1.
4. A hypolipidemic agent comprising a bile acid derivative as claimed in claim 1.
* * * * *

UNITED STATES PATENT AND TRADEMARK OFFICE
CERTIFICATE OF CORRECTION

PATENT NO. : 5,610,151
DATED : March 11, 1997
INVENTOR(S) : Heiner GLOMBIK et al.

It is certified that error appears in the above-indentified patent and that said Letters Patent is hereby corrected as shown below:

Claim 1, column 32, line 31, delete "or - N $\neq R \neq_3$".

Signed and Sealed this

Seventh Day of October, 1997

Attest:

BRUCE LEHMAN

Attesting Officer

Commissioner of Patents and Trademarks